(12) United States Patent
Pei

(10) Patent No.: US 10,967,187 B2
(45) Date of Patent: Apr. 6, 2021

(54) METHOD AND DEVICE FOR MANAGING A SELF-TERMINATION PERIOD FOR VENTRICULAR ARRHYTHMIAS

(71) Applicant: PACESETTER, INC., Sylmar, CA (US)

(72) Inventor: Xing Pei, Thousand Oaks, CA (US)

(73) Assignee: PACESETTER, INC., Sylmar, CA (US)

(*) Notice: Subject to any disclaimer, the term of this patent is extended or adjusted under 35 U.S.C. 154(b) by 331 days.

(21) Appl. No.: 15/829,269

(22) Filed: Dec. 1, 2017

(65) Prior Publication Data

US 2019/0168003 A1    Jun. 6, 2019

(51) Int. Cl.
*A61N 1/36* (2006.01)
*A61N 1/365* (2006.01)
(Continued)

(52) U.S. Cl.
CPC .......... *A61N 1/36514* (2013.01); *A61B 5/316* (2021.01); *A61B 5/361* (2021.01);
(Continued)

(58) Field of Classification Search
CPC .............. A61N 1/36514; A61N 1/3621; A61N 1/36592; A61N 1/3925; A61N 1/3956; A61N 1/3987; A61N 1/025; A61N 1/0587; A61N 1/3605; A61N 1/3622; A61N 1/3706; A61N 1/3756; G16H 50/20; G16H 40/63;
(Continued)

(56) References Cited

U.S. PATENT DOCUMENTS 5,978,707 A    11/1999   Krig et al.
7,103,404 B2   9/2006    Stadler et al.
(Continued)

FOREIGN PATENT DOCUMENTS

EP         1804913 B1    7/2011

OTHER PUBLICATIONS

Extended EP Search Report dated Feb. 26, 2019—Counterpart EP Pat. App. 18209359.1.

*Primary Examiner* — Catherine M Voorhees
*Assistant Examiner* — Roland Dinga
(74) *Attorney, Agent, or Firm* — The Small Patent Law Group LLC; Dean D. Small

(57) ABSTRACT

Methods and devices are provided for sensing cardiac events from electrodes located proximate to one or more atrial or ventricular sites, over a period of time that includes a detection period followed by an observation period. One or more processors declare a ventricular arrhythmia episode and a corresponding VT/VF therapy based on the cardiac events during at least the detection period. The processors delay delivery of the VT/VF therapy for a self-termination period within the observation period. The self-termination period represents a time period during which the ventricular arrhythmia episode may self-terminate. The processors analyze a stability characteristic of interest (COI) from the cardiac events sensed over at least a portion the observation period and determine an end point for the self-termination period, within the observation period, based on the stability COI. The VT/VF therapy is delivered when the VT/VF arrhythmia episode continues past the end point.

28 Claims, 11 Drawing Sheets

(51) Int. Cl.
    *G16H 20/10* (2018.01)
    *G16H 50/20* (2018.01)
    *G16H 40/63* (2018.01)
    *A61B 5/00* (2006.01)
    *A61B 5/316* (2021.01)
    *A61B 5/361* (2021.01)
    *A61B 5/363* (2021.01)
    *A61N 1/362* (2006.01)
    *A61N 1/39* (2006.01)
    *A61N 1/375* (2006.01)
    *A61N 1/37* (2006.01)
    *A61N 1/05* (2006.01)
    *A61N 1/02* (2006.01)

(52) U.S. Cl.
    CPC ............ *A61B 5/363* (2021.01); *A61B 5/4836* (2013.01); *A61B 5/686* (2013.01); *A61N 1/3621* (2013.01); *A61N 1/36592* (2013.01); *A61N 1/3925* (2013.01); *A61N 1/3956* (2013.01); *A61N 1/3987* (2013.01); *G16H 20/10* (2018.01); *G16H 40/63* (2018.01); *G16H 50/20* (2018.01); *A61B 5/0006* (2013.01); *A61B 5/0031* (2013.01); *A61N 1/025* (2013.01); *A61N 1/0587* (2013.01); *A61N 1/3605* (2013.01); *A61N 1/3622* (2013.01); *A61N 1/3706* (2013.01); *A61N 1/3756* (2013.01)

(58) Field of Classification Search
    CPC .... G16H 20/10; A61B 5/04012; A61B 5/046; A61B 5/0464; A61B 5/4836; A61B 5/686; A61B 5/0006; A61B 5/0031
    See application file for complete search history.

(56) References Cited

U.S. PATENT DOCUMENTS

| | | |
|---|---|---|
| 8,391,980 B2 | 3/2013 | Bornzin et al. |
| 8,831,747 B1 | 9/2014 | Min et al. |
| 9,044,610 B2 | 6/2015 | Rosenberg et al. |
| 9,216,285 B1 | 12/2015 | Boling et al. |
| 9,232,485 B2 | 1/2016 | Wu et al. |
| 9,333,351 B2 | 5/2016 | Arnold et al. |
| 2003/0204209 A1* | 10/2003 | Burnes ................ A61N 1/3621 607/14 |
| 2009/0270933 A1* | 10/2009 | Hettrick ............... A61B 5/0535 607/6 |
| 2010/0317984 A1 | 12/2010 | McCarthy et al. |
| 2018/0318588 A1* | 11/2018 | Dennis ................ A61B 5/4836 |

\* cited by examiner

METHOD AND DEVICE FOR MANAGING A SELF-TERMINATION PERIOD FOR VENTRICULAR ARRHYTHMIAS

BACKGROUND

Embodiments of the present disclosure generally relate to methods and devices for treating ventricular (VT/VF) arrhythmias and more particularly to methods and devices that manage self-termination periods before delivering VT/VF therapy.

Ventricular tachycardia may be controlled through electrical therapy delivered by an implanted medical device, such as a pacemaker portion of an ICD, implantable cardioverter defibrillator and the like. The device applies an electric stimulation to the heart muscle to interrupt or disrupt the fast rhythm. The electric stimulation may be in the form of timed pacemaker pulses or by high voltage shock. Antitachycardia pacing (ATP) has been used to convert a ventricular tachycardia into a normal sinus rhythm. Tachycardia/fibrillation is often the result of electrical feedback within the heart and/or irregular fast beats, wherein a natural beat results in the feedback of an electrical stimulus which prematurely triggers another beat. By interposing a stimulated heartbeat (i.e., a pacing pulse), the stability of the feedback loop is disrupted. For example, patients with monomorphic ventricular tachycardia (MVT) may be successfully paced out of the tachycardia using a rapid burst of high rate pacing. The burst includes a selected number of pulses that are delivered at the same rate, at an accelerating rate, or an alternating accelerating/decelerating rate.

Ventricular tachy therapies, either anti-tachycardia pacing or high voltage shocking, or combination thereof, are delivered after the tachycardia episode is detected and classified. Recently, it has been suggested that ventricular tachycardia or fibrillation episodes may self-terminate if the device allows time for the episode to self-terminate. There is increasing awareness that unnecessary, even appropriate, therapies may have undesired clinical effects.

Further, a prevalent concern remains that extending the detection interval will increase syncopal events due to delay in therapy for hemodynamically compromising ventricular arrhythmias. Therefore, there are conflicts between the goals to terminate dangerous ventricular arrhythmia early, versus delaying therapy to see if the ventricular arrhythmia can self-terminate without therapeutic treatment.

Heretofore, it has been proposed to prolong the detection interval by a predefined amount (e.g., increase the number detection intervals before making a treatment decision). However, simply extending the detection interval may not optimally address the clinical needs. By increasing the detection interval by a set number of cardiac cycles, the IMD extends the detection time period before a therapy is delivered. During the extended detection time period, the IMD allows for self-termination to occur. However, during the extended time period, in the event that the arrhythmia exhibits a behavior that would be normally considered dangerous, the IMD will not provide treatment. Instead, treatment is delayed for the set number of cardiac cycles regardless of the nature of the arrhythmia.

SUMMARY

In accordance with embodiments herein a method, is provided comprising sensing cardiac events from electrodes located proximate to one or more atrial or ventricular sites, over a period of time that includes a detection period followed by an observation period. The method includes utilizing one or more processors to declare a ventricular arrhythmia episode and a corresponding VT/VF therapy based on the cardiac events during at least the detection period. The method further includes delaying delivery of the VT/VF therapy for a self-termination period within the observation period, the self-termination period representing a time period during which the ventricular arrhythmia episode may self-terminate and analyzing a stability characteristic of interest (COI) from the cardiac events sensed over at least a portion the observation period. The method further determines an end point for the self-termination period, within the observation period, based on the stability COI; and delivers the VT/VF therapy when the VT/VF arrhythmia episode continues past the end point.

Additionally or alternatively, the analyzing and determining operations may occur in response to the declaring of the VT/VF therapy and after the delaying delivery of the VT/VF therapy. The analyzing operation may further comprise detecting tachycardia events from the cardiac events, measuring amplitudes of the tachycardia events, and analyzing the stability COI based on the amplitudes. The analyzing operation may further comprise calculating the stability COI based on at least one of a mean or variance of the amplitudes.

The analyzing operation may further comprise detecting tachycardia events from the cardiac events, measuring rates between the tachycardia events, and analyzing the stability COI based on the rates. The analyzing operation further may comprise calculating the stability COI based on at least one of a mean or variance of the rates. The determining operation ends the self-termination period when the stability COI exhibits increasing rate instability and initiates an operation to deliver the VT/VF therapy.

The stability COI may represent a degree of variation in at least one of an amplitude or rate of the tachycardia events, the analyzing operation declaring the tachycardia events to be stable or unstable based on the stability COI. When the stability COI is declared stable, the determining operation sets the end point based on a predetermined maximum duration for the self-termination period before delivering the VT therapy. If the stability COI is declared unstable when the degree of variation corresponds to a rate variation that exceeds a rate threshold, the method further comprises determining whether the rate variation represents increasing or decreasing rate instability, the determining operation setting the end point based on a predetermined maximum duration for the self-termination period before delivering the VT therapy when the stability COI exhibits the decreasing rate instability. If the stability COI is declared unstable when the stability COI indicates the degree of variation in the amplitude exceeds an amplitude threshold, the method further comprising determining whether the amplitude exhibits increasing or decreasing amplitude instability, wherein the determining operation designating the end point for the self-termination period when the stability COI exhibits the increasing amplitude instability and initiates an operation to deliver the VT/VF therapy.

The analyzing operation may determine whether the stability COI is stable or unstable and increasing or decreasing, the determining operation designating a first end point for the self-termination period when the stability COI exhibits an unstable and decreasing rate in combination with an unstable amplitude. The method may comprise maintaining an arrhythmia self-termination log that is utilized in connection with a self-learning process to recognize certain types of arrhythmias as either self-terminating or non-self-terminating.

In accordance with embodiments herein, an implantable medical device is provided, comprised of electrodes configured to be located proximate to one or more atrial or ventricular sites, the electrodes configured to sense cardiac events over a period of time that includes a detection period followed by an observation period. The device may be comprised of memory to store program instructions; and one or more processors that, when executing the program instructions: declare a ventricular arrhythmia episode and a corresponding VT/VF therapy based on the cardiac events during at least the detection period. The processors may delay delivery of the VT/VF therapy for a self-termination period within the observation period, the self-termination period representing a time period during which the ventricular arrhythmia episode may self-terminate. They may analyze a stability characteristic of interest (COI) from the cardiac events sensed over at least a portion the observation period, determine an end point for the self-termination period, within the observation period, based on the stability COI; and deliver the VT/VF therapy when the VT/VF arrhythmia episode continues past the end point.

The one or more processors may be configured to perform the analyze and determine operations occur in response to the declaring of the VT/VF therapy and after the delaying delivery of the VT/VF therapy. The one or more processors may be further configured to detect tachycardia events from the cardiac events, measure amplitudes of the tachycardia events, and analyze the stability COI based on the amplitudes. The one or more processors may further configured to calculate the stability COI based on at least one of a mean or variance of the amplitudes.

The one or more processors may further be configured to detect tachycardia events from the cardiac events, measure rates between the tachycardia events, and analyze the stability COI based on the rates. The one or more processors may be configured to determine whether past and current ventricular arrhythmia episodes are similar and based thereon declaring the current ventricular arrhythmia episode to be self-terminating. The one or more processors may adjust a duration of the observation period based on whether the current ventricular arrhythmia episode is declared to be self-terminating.

DETAILED DESCRIPTION

Figure 1A:
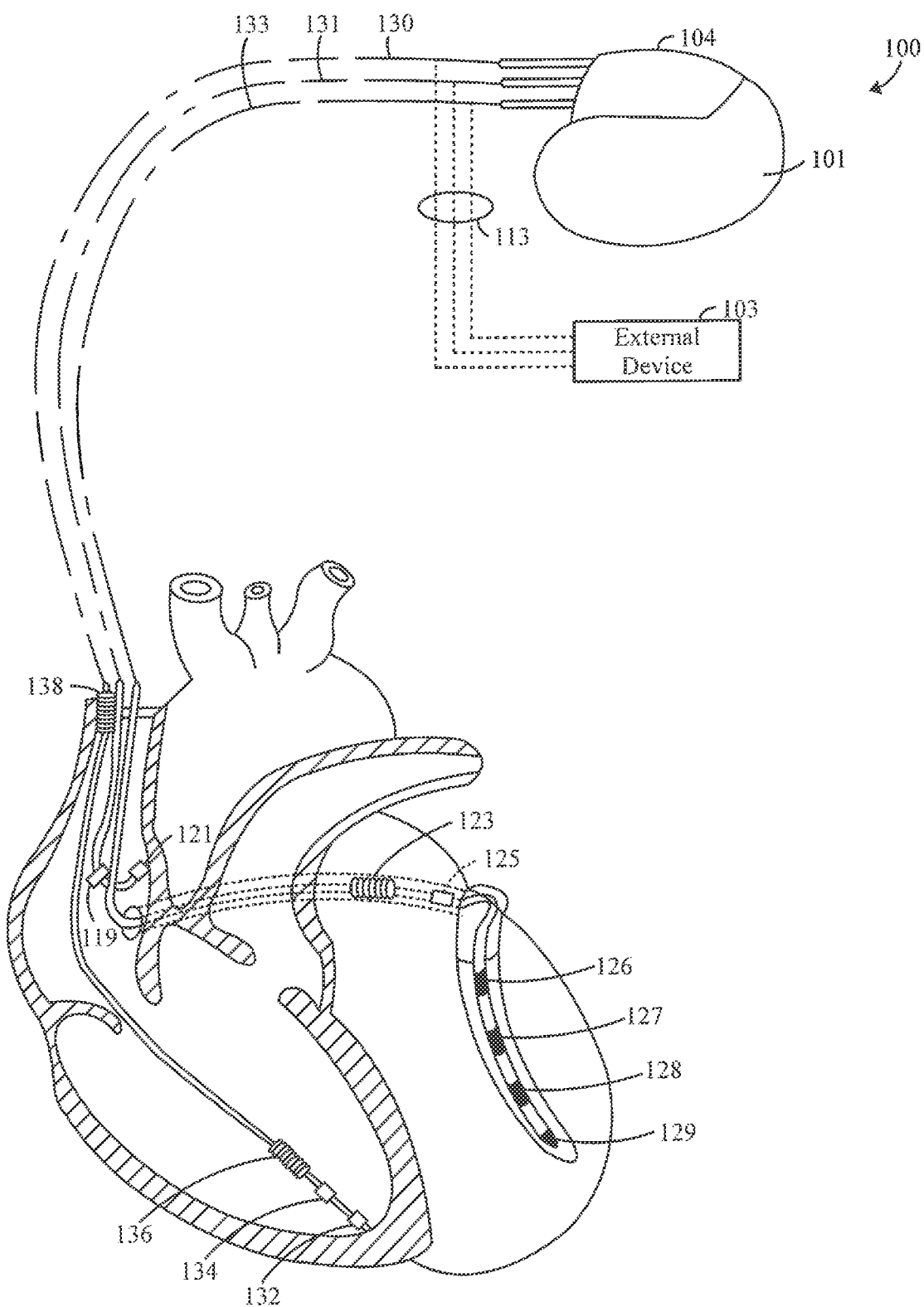
FIG. 1A illustrates an IMD and external device coupled to a heart in a patient and implemented in accordance with one embodiment.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

The methods and systems described herein may employ all or portions of structures or aspects of various embodiments discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, where indicated, the methods may be fully or partially implemented by one or more processors of one or more devices or systems. While the operations of some methods may be described as performed by the processor(s) of one device, additionally, some or all of such operations may be performed by the processor(s) of another device described herein.

In accordance with embodiments herein, methods and systems are described that address the needs for timely detection of ventricular arrhythmias but with an added observation period to perform analysis on a rhythm and to determine a preferred (e.g., optimal) treatment time. In addition, embodiments herein provide for self-learning to determine whether one or more types of rhythm should be treated earlier or later. By way of example, embodiments herein define a quick detection period (e.g., when performing traditional tachyarrhythmia detection), and an observation and analysis period, to address certain conflicting goals such as i) a dangerous rhythm needs to be detected early whereas ii) therapy may be delayed to see if the ventricular arrhythmia can self-terminate without therapeutic treatment. In addition, embodiments perform self-learning in connection with determining which type(s) of rhythm warrant treatment earlier rather than later. During the observation and analysis period, the methods and systems herein determine if a therapy should be delivered quickly or the process can wait longer based on the type of ventricular arrhythmia, the arrhythmia progression, and a learned history of similar types of ventricular arrhythmia.

Implantable Medical Device

FIG. 1A illustrates an IMD 100 and external device 103 coupled to a heart in a patient and implemented in accordance with one embodiment. The external device 103 may be a programmer, an external defibrillator, a workstation, a portable computer, a personal digital assistant, a cell phone, a bedside monitor and the like. The IMD may represent a cardiac monitoring device, pacemaker, cardioverter, cardiac rhythm management device, defibrillator, neurostimulator, leadless monitoring device, leadless pacemaker and the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a housing 101 that is joined to a header assembly that holds receptacle connectors connected to a right ventricular lead 130, a right atrial lead 131, and a coronary sinus lead 133, respectively. The leads 131, 124 and 130 measure cardiac signals of the heart. The right atrial lead 131 includes an atrial tip electrode 121 and an atrial ring electrode 119. The coronary sinus lead 133 includes a left atrial ring electrode 123, a left atrial coil electrode 125 and one or more left ventricular electrodes 126-129 (e.g., also referred to as P1, M1, M2 and D1) to form a multi-pole LV electrode combination. The right ventricular lead 130 includes an RV tip electrode 132, an RV ring electrode 134, an RV coil electrode 136, and an SVC coil electrode 138. The leads 131, 124 and 130 detect IEGM signals that are processed and analyzed as described herein. The leads 131, 124 and 130 also delivery therapies as described herein.

During implantation, the external device 103 is connected to one or more of the leads 131, 124 and 130 through temporary inputs 113. The inputs 113 of the external device 103 receive IEGM signals from the leads 131, 124 and 130 during implantation and display the IEGM signals to the physician on a display. Optionally, the external device 103 may not be directly connected to the leads 131, 124 and 130. Instead, the IEGM cardiac signals sensed by the leads 131, 124 and 130 may be collected by the IMD 100 and then transmitted wirelessly to the external device 103. Hence, the external device 103 receives the IEGM cardiac signals through telemetry circuit inputs. The physician or another user controls operation of the external device 103 through a user interface.

Figure 1B:
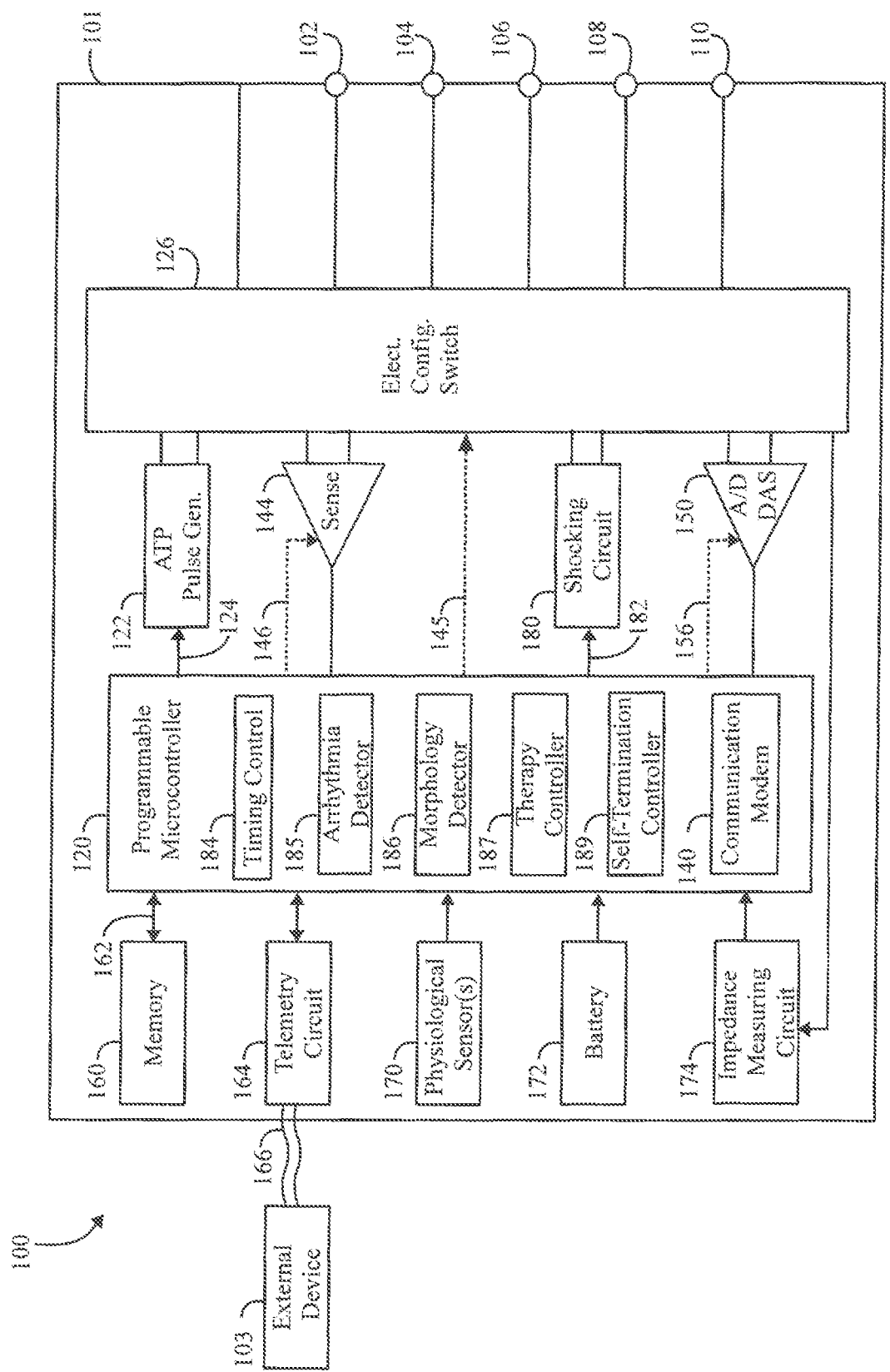
FIG. 1B shows a block diagram of an example IMD that is implanted into the patient as part of the implantable cardiac system.

FIG. 1B shows a block diagram of an example IMD 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing.

The IMD 100 has a housing 101 to hold the electronic/computing components. The housing 101 (which is often referred to as the "can", "case", "encasing", or "case electrode") may be programmably selected to act as the return electrode for certain stimulus modes. The housing 101 further includes a connector (not shown) with a plurality of terminals 102, 104, 106, 108, and 110. The terminals may be connected to electrodes that are located in various locations within and about the heart. For example, the terminals may include: a terminal 102 to be coupled to an first electrode (e.g., a tip electrode) located in a first chamber; a terminal 104 to be coupled to a second electrode (e.g., tip electrode) located in a second chamber; a terminal 106 to be coupled to an electrode (e.g. ring) located in the first chamber; a terminal 108 to be coupled to an electrode located (e.g., ring electrode) in the second chamber; and a terminal 110 to be coupled to an electrode (e.g., coil) located in the SVC. The type and location of each electrode may vary. For example, the electrodes may include various combinations of ring, tip, coil and shocking electrodes and the like.

The IMD 100 includes a programmable microcontroller 120 that controls various operations of the IMD 100, including cardiac monitoring and stimulation therapy. Microcontroller 120 includes a microprocessor (or equivalent control circuitry), RAM and/or ROM memory, logic and timing circuitry, state machine circuitry, and I/O circuitry.

IMD 100 further includes a pulse generator 122 that generates stimulation pulses (e.g., anti-tachycardia or ATP pacing) for delivery by one or more electrodes coupled thereto. The pulse generator 122 is controlled by the microcontroller 120 via control signal 124. The pulse generator 122 is coupled to the select electrode(s) via an electrode configuration switch 126, which includes multiple switches for connecting the desired electrodes to the appropriate I/O circuits, thereby facilitating electrode programmability. The switch 126 is controlled by a control signal 145 from the microcontroller 120.

In the example of FIG. 1B, a single pulse generator 122 is illustrated. Optionally, the IMD 100 may include multiple pulse generators, similar to pulse generator 122, where each pulse generator is coupled to one or more electrodes and controlled by the microcontroller 120 to deliver select stimulus pulse(s) to the corresponding one or more electrodes.

Microcontroller 120 is illustrated to include timing control circuitry 184 to control the timing of the stimulation pulses (e.g., pacing rate, atrio-ventricular (AV) delay, atrial inter-conduction (A-A) delay, or ventricular inter-conduction (V-V) delay, etc.). The timing control circuitry 184 may also be used for the timing of refractory periods, blanking intervals, noise detection windows, evoked response windows, alert intervals, marker channel timing, and so on. Microcontroller 120 also has an arrhythmia detector 185 for detecting arrhythmia conditions and a morphology detector 186 to review and analyze one or more features of the morphology of cardiac signals. Although not shown, the microcontroller 120 may further include other dedicated circuitry and/or firmware/software components that assist in monitoring various conditions of the patient's heart and managing pacing therapies.

The arrhythmia detector 185 and/or morphology detector 186 analyze the cardiac signals indicative of cardiac events that are sensed by electrodes located proximate to one or more atrial and/or ventricular sites. The cardiac events are sensed over a period of time that includes a detection period followed by an observation period as discussed further herein. The arrhythmia and/or morphology detectors 185 and 186 analyze the cardiac events in accordance with conventional ventricular arrhythmia algorithms, such as conventional tachycardia detection algorithms and/or fibrillation detection algorithms. Based on the analysis, the arrhythmia and/or morphology detectors 185 and 186 declare a ventricular arrhythmia episode, such as SVT block, a ventricular tachycardia episode or a ventricular fibrillation episode, collectively VT/VT arrhythmias.

The microcontroller 120 includes a therapy controller 187 and a self-termination controller 189. The therapy controller 187 manages delivery of ventricular (VT) therapies based upon the type of arrhythmia detected. For example, in connection with certain types of arrhythmias, the therapy controller 187 may direct delivery of a ventricular ATP therapy through pulse generator 122 based upon predetermined ATP therapy parameters. Additionally or alternatively, the therapy controller 187 may direct delivery of a ventricular high voltage shock by shocking circuit 180 based upon predetermined high-voltage shock therapy parameters.

In accordance with embodiments herein, the self-termination controller 189 delays delivery of the VT therapy for a self-termination period. The self-termination period occurs within the observation period and represents a time period during which the ventricular arrhythmia episode may self-terminate. The self-termination controller 189 analyzes one or more stability characteristics of interest (COI) for the cardiac events that are sensed over at least a portion of the observation period. Additionally and/or alternatively, cardiac events sensed during the detection period may also be analyzed in connection with determining a stability COI. The self-termination controller 189 determines an end point for the self-termination period based on the stability COI. The self-termination controller 189 analyzes the stability COI and determines the duration and endpoint of the self-termination period after the original VT/VF therapy has been delayed (e.g., during the observation period). The endpoint for the self-termination period may occur at an intermediate point within the observation period and/or proximate to, or contemporaneous with, the end of the observation period. Once the endpoint occurs, arrhythmia detector and/or morphology detector 185 and 186 determine whether the VT/VF arrhythmia episode continues. The VT/VF therapy controller 187 delivers the VT/VF therapy in the event that the VT/VF arrhythmia episode continues past the endpoint of the self-termination period.

The self-termination controller 189 manages the duration of the self-termination period and delays delivery of the VT therapy based on various aspects of the stability COI. In accordance with embodiments herein, the self-termination controller 189 may detect tachycardia events from the cardiac events, measure amplitudes of the tachycardia events and analyze the stability COI based on the amplitudes. For example, the stability COI may be calculated based on at least one of a mean, average, variance or other statistical characteristic of the amplitudes of the tachycardia events measured. Additionally or alternatively, the self-termination controller 189 may measure rates between successive tachycardia events and analyze the stability COI based on the rates. For example, the stability COI may be calculated based on at least one of a mean, average, variance or other statistical characteristic of the measured rates.

As explained herein, the self-termination controller 189 may end the self-termination period when the stability COI exhibits an increasing rate instability. In connection therewith, the therapy controller 187 initiates an operation to deliver a VT/VF therapy. The initiation of the VT/VF therapy may merely represent delivering ATP pacing in accordance with predetermined parameters. Additionally or alternatively, initiation of the VT/VF therapy may correspond to initiating a charging operation for a high-voltage charging circuit. Once the high-voltage charging circuit is charged to a desired level, the charge is discharged as a high-voltage shock. Optionally, the high-voltage charging circuit may begin at an earlier point in time to ensure timely treatment at an end of the observation period.

The stability COI represents a degree of variation in one or more of an amplitude or rate of tachycardia events. The COI may be continuously monitored. The rate and/or amplitude of the tachycardia events may exhibit a stable or unstable pattern/behavior. The degree of variation in the amplitude and/or rate of the tachycardia events may increase or decrease over the duration of a VT/VF arrhythmia episode. When the self-termination controller 189 declares the stability COI to be stable, the self-termination controller 189 sets the end point based on a predetermined maximum duration for the self-termination, before delivering the VT/VF therapy. The self-termination controller 189 declares the stability COI unstable when the degree of variation corresponds to a rate variation that exceeds a rate threshold. In connection there with, the self-termination controller 189 determines whether the rate variation represents increasing or decreasing rate instability, and sets the end point based on a predetermined maximum duration for the self-termination period before delivering the VT/VF therapy when the stability COI exhibits the decreasing rate instability.

Additionally or alternatively, the self-termination controller 189 declares the stability COI unstable when the stability COI indicates that the degree of variation in the amplitude exceeds an amplitude variation threshold. In connection there with, the self-termination controller 189 determines whether the amplitude exhibits increasing or decreasing amplitude instability, and designates the end point for the self-termination period when the stability COI exhibits the increasing amplitude instability and initiates an operation to deliver the VT/VF therapy. Additionally or alternatively, the self-termination controller 189 determines whether the stability COI is stable or unstable and increasing or decreasing. The self-termination controller 189 designates a first end point for the self-termination period when the stability COI exhibits an unstable and decreasing rate in combination with an unstable amplitude. Additionally or alternatively, the self-termination controller 189 determines whether the stability COI is stable or unstable and increasing or decreasing. The self-termination controller 189 designates a second end point for the self-termination period when the stability COI exhibits an unstable and increasing rate.

The IMD 100 is further equipped with a communication modem (modulator/demodulator) 140 to enable wireless communication with other devices, implanted devices and/or external devices. In one implementation, the communication modem 140 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 140 may be implemented in hardware as part of the microcontroller 120, or as software/firmware instructions programmed into and executed by the microcontroller 120. Alternatively, the modem 140 may reside separately from the microcontroller as a standalone component.

The IMD 100 includes sensing circuitry 144 selectively coupled to one or more electrodes that perform sensing operations, through the switch 126 to detect the presence of cardiac activity in the right chambers of the heart. The sensing circuitry 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 102 to sense low amplitude signal characteristics of atrial fibrillation. Switch 126 determines the sensing polarity of the cardiac signal by selectively closing the appropriate switches. In this way, the clinician may program the sensing polarity independent of the stimulation polarity.

The output of the sensing circuitry 144 is connected to the microcontroller 120 which, in turn, triggers or inhibits the pulse generator 122 in response to the absence or presence of cardiac activity. The sensing circuitry 144 receives a control signal 146 from the microcontroller 120 for purposes of controlling the gain, threshold, polarization charge removal circuitry (not shown), and the timing of any blocking circuitry (not shown) coupled to the inputs of the sensing circuitry.

In the example of FIG. 1B, a single sensing circuit 144 is illustrated. Optionally, the IMD 100 may include multiple sensing circuit, similar to sensing circuit 144, where each sensing circuit is coupled to one or more electrodes and controlled by the microcontroller 120 to sense electrical activity detected at the corresponding one or more electrodes. The sensing circuit 144 may operate in a unipolar sensing configuration or in a bipolar sensing configuration.

The IMD 100 further includes an analog-to-digital (A/D) data acquisition system (DAS) 150 coupled to one or more electrodes via the switch 126 to sample cardiac signals across any pair of desired electrodes. The data acquisition system 150 is configured to acquire intracardiac electrogram signals, convert the raw analog data into digital data, and store the digital data for later processing and/or telemetric transmission to an external device 103 (e.g., a programmer, local transceiver, or a diagnostic system analyzer). The data acquisition system 150 is controlled by a control signal 156 from the microcontroller 120.

The microcontroller 120 is coupled to a memory 160 by a suitable data/address bus 162. The programmable operating parameters used by the microcontroller 120 are stored in memory 160 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 100 may be non-invasively programmed into the memory 160 through a telemetry circuit 164 in telemetric communication via communication link 166 with the external device 103. The telemetry circuit 164 allows intracardiac electrograms and status information relating to the operation of the IMD 100 (as contained in the microcontroller 120 or memory 160) to be sent to the external device 103 through the established communication link 166.

The IMD 100 can further include magnet detection circuitry (not shown), coupled to the microcontroller 120, to detect when a magnet is placed over the unit. A magnet may be used by a clinician to perform various test functions of the IMD 100 and/or to signal the microcontroller 120 that the external programmer 103 is in place to receive or transmit data to the microcontroller 120 through the telemetry circuits 164.

The IMD 100 can further include one or more physiologic sensors 170. Such sensors are commonly referred to as "rate-responsive" sensors because they are typically used to adjust pacing stimulation rates according to the exercise state of the patient. However, the physiological sensor 170 may further be used to detect changes in cardiac output, changes in the physiological condition of the heart, or diurnal changes in activity (e.g., detecting sleep and wake states). Signals generated by the physiological sensors 170 are passed to the microcontroller 120 for analysis. The microcontroller 120 responds by adjusting the various pacing parameters (such as rate, AV Delay, V-V Delay, etc.) at which the atrial and ventricular pacing pulses are administered. While shown as being included within the IMD 100, the physiologic sensor(s) 170 may be external to the IMD 100, yet still be implanted within or carried by the patient. Examples of physiologic sensors might include sensors that, for example, sense respiration rate, pH of blood, ventricular gradient, activity, position/posture, minute ventilation (MV), and so forth.

A battery 172 provides operating power to all of the components in the IMD 100. The battery 172 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 172 also desirably has a predictable discharge characteristic so that elective replacement time can be detected. As one example, the IMD 100 employs lithium/silver vanadium oxide batteries.

The IMD 100 further includes an impedance measuring circuit 174, which can be used for many things, including: lead impedance surveillance during the acute and chronic periods for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 174 is coupled to the switch 126 so that any desired electrode may be used.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 120 further controls a shocking circuit 180 by way of a control signal 182. The shocking circuit 180 generates shocking pulses of low (e.g., up to 0.5 joules), moderate (e.g., 0.5-10 joules), or high energy (e.g., 111 to 40 joules), as controlled by the microcontroller 120. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Self-Termination Period Management Process

Figure 2:
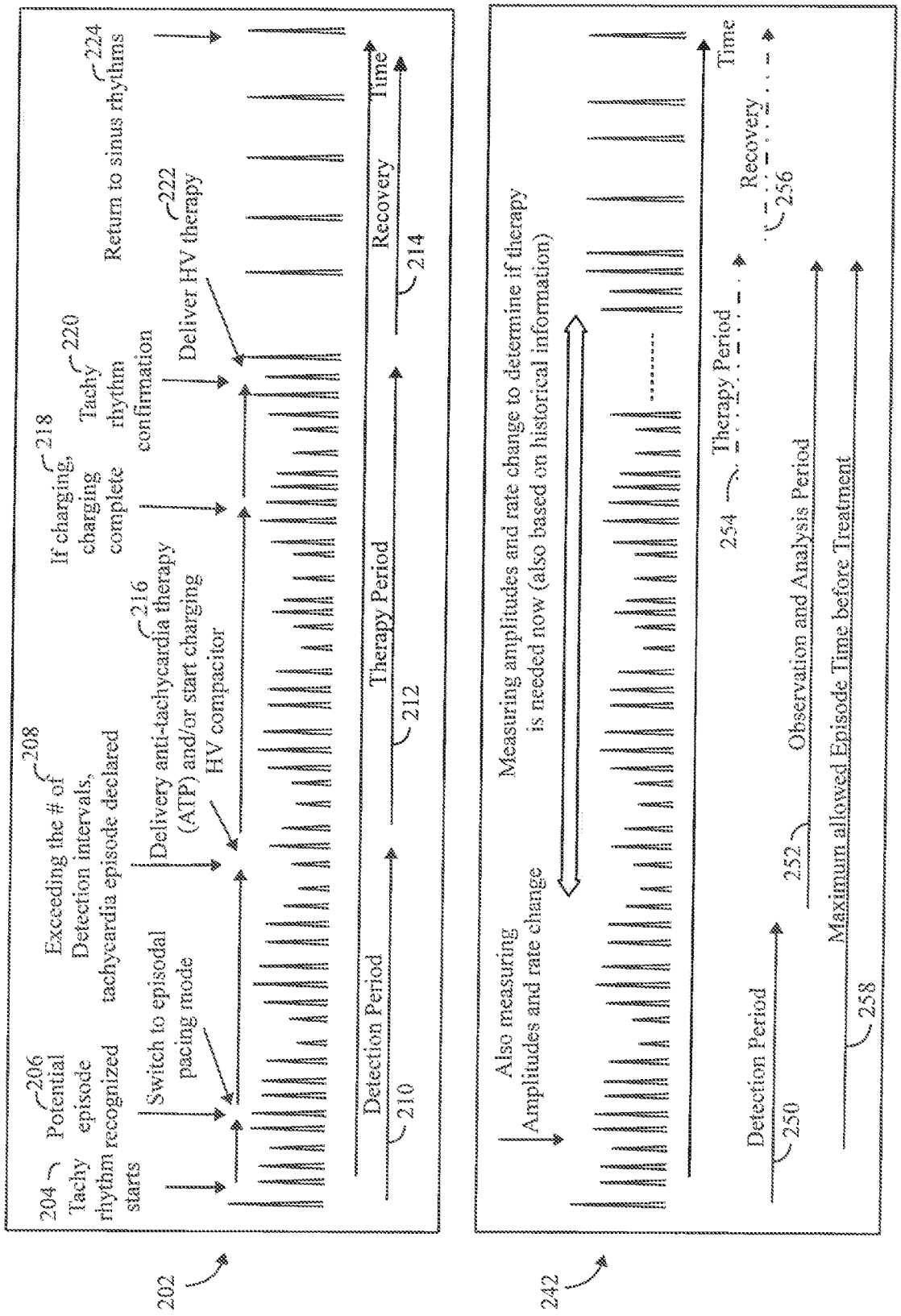
FIG. 2 illustrates examples of cardiac signals corresponding to cardiac events that are analyzed in connection with detecting arrhythmias of interest and delivering corresponding therapies by an IMD.

FIG. 2 illustrates examples of cardiac signals corresponding to cardiac events that are analyzed in connection with detecting arrhythmias of interest and delivering corresponding therapies by an IMD. An upper panel 202 illustrates cardiac events corresponding to a tachyarrhythmia episode. The sequence of cardiac events in the upper panel 202 is divided into a detection period 210, a therapy period 212 and a recovery period 214. At 204, the tachycardia rhythm starts. At 206, a candidate or potential tachycardia episode is recognized by the arrhythmia detection and/or morphology detection algorithms. Optionally, in response thereto, the IMD switches to an episodal pacing mode. At 208, the IMD determines that the number of tachycardia events have exceeded a predetermined number during a detection interval, and declares a tachycardia episode. At 216, the IMD delivers ATP therapy and/or begins charging a high-voltage charging circuit in preparation for delivery of a high voltage shock. At 218, the charging operation is complete. At 220, the IMD again confirms that the tachyarrhythmia continues and when the tachyarrhythmia continues, the IMD delivers a high-voltage therapy at 222. In response thereto, the cardiac rhythm returned to a normal sinus rhythm as noted at 224.

Optionally, the IMD may apply various discriminators to address other fast rate arrhythmias of interest, such as supraventricular tachyarrhythmia (SVT). When the arrhythmia is not SVT, the IMD will deliver a programmed tachy therapy, such as an ATP pacing therapy or a high-voltage shock or a combination thereof. The IMD delivers the tachy therapy until the arrhythmia is converted back to a normal sinus rhythm or until a time period allowed for therapy is exhausted based on a programmed configuration of the IMD.

The panel 242 of FIG. 2 illustrates cardiac events corresponding to a tachyarrhythmia episode, but with the sequence of cardiac events divided into a detection period 250, an observation and analysis period 252, a therapy period 254 and a recovery period 256. During the detection period 250, the IMD operates in the same manner as described in connection with the panel 202 to identify a tachycardia episode. The IMD delays delivery of the therapy (e.g., the therapy at 216 and/or the therapy at 222). The IMD sets a predetermined maximum duration 258 which may represent a maximum self-termination duration allowed before delivering the VT/VF therapy. In accordance with embodiments herein, the IMD analyzes stability characteristics of interest from the tachycardia events during the observation period 252.

After a ventricular tachyarrhythmia starts, the IMD detects the fast rate of the rhythm during the detection period 250. The IMD enters an episodal pacing mode to allow for better sensing of ventricular signals. During the detection period, the IMD detects and counts the number of tachycardia events and intervals there between. The IMD measures amplitudes of the detected events, as well as intervals between detected events. As explained herein, the IMD calculates a mean and variance between the measured amplitudes over the detection period. The IMD also calculates a mean and variance between the intervals between events over the detection period. At termination of the detection period, the IMD enters an observation and analysis period. During the observation and analysis period 252, the IMD continues to detect and count the number of tachy events and intervals there between. The IMD measures amplitudes of the detected events, as well as intervals between detected events over the observation and analysis period. As explained herein, the IMD calculates a mean and variance between the measured amplitudes over the detection period. The IMD also calculates a mean and variance between the intervals between events over the detection period. Additionally or alternatively, the IMD may calculate the mean and variance based on events and intervals detected over the combination of the detection period and the observation and analysis period.

Next, example implementations of the observation and analysis period are described in connection with FIGS. 3A-3E. FIGS. 3A-3E illustrate a common detection period 310, followed by a common observation and analysis period 312. For purposes of illustration, during the detection period 310 of each of FIGS. 3A-3E, a tachycardia episode is declared at 308, and a predetermined maximum self-determination duration 358 is defined. FIGS. 3A-3E illustrate different examples of how the stability characteristic of interest may vary, and based thereon, the IMD manages the self-termination duration in different corresponding manners. During the observation and analysis period 312, the IMD delays therapy for the self-termination period while measuring signal amplitudes and variations there between. The IMD analyzes variations in rate and amplitude, and based on the variations, determine a duration of the self-termination period 358, thereby determining whether a therapy should be started or delayed.

Figure 3A:
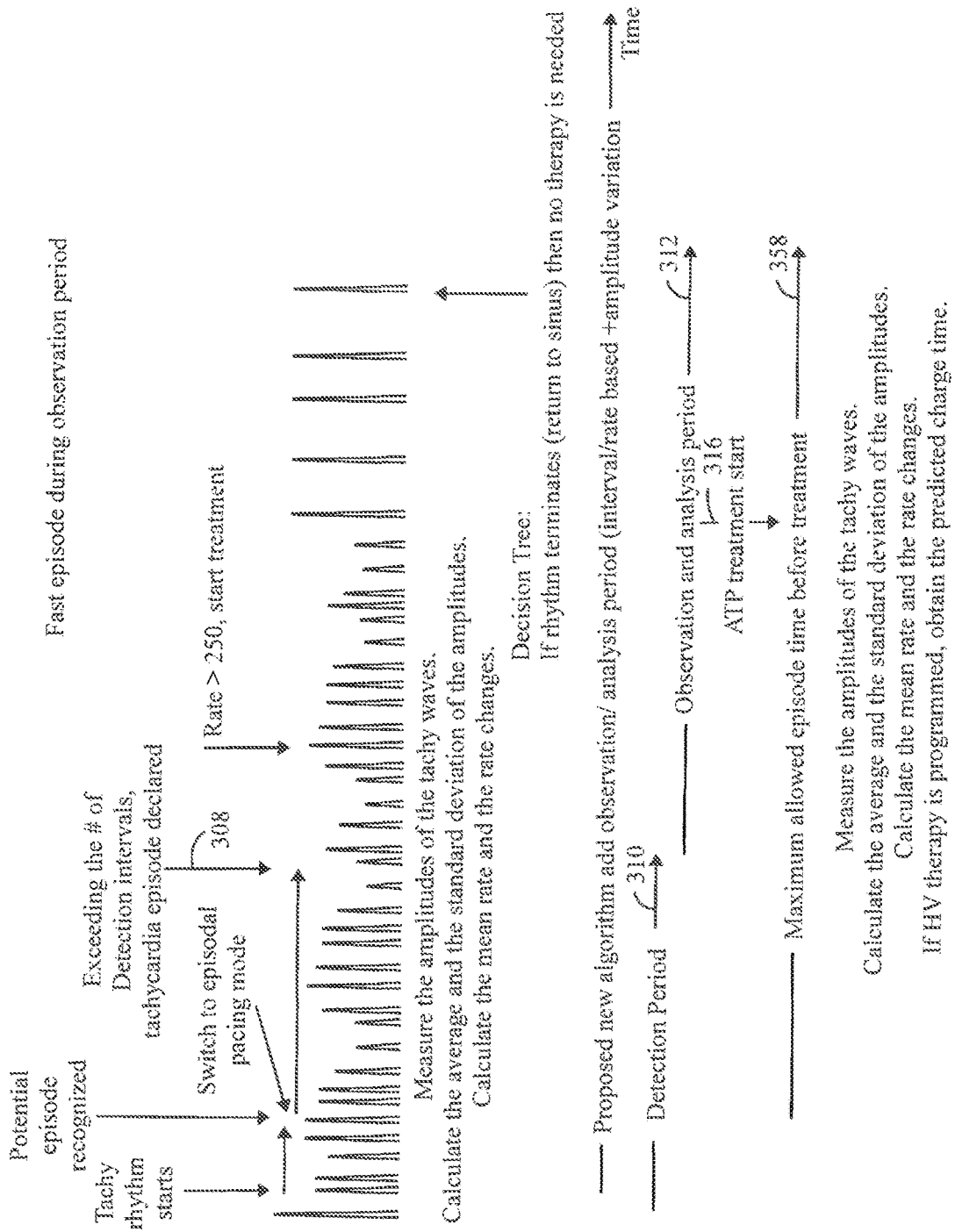
FIG. 3A illustrates an example in which the process applies one or more threshold criteria, such as a rate based criteria.

FIG. 3A illustrates an example in which the process applies one or more threshold criteria, such as a rate based criteria. For example, the process may determine whether events are occurring at a rate higher than an upper threshold (e.g., at or above 250 bpm). The rate at which events occur may be analyzed during the detection period and/or during the observation and analysis period. When the event rate exceeds an upper threshold, the IMD may start the therapy. Alternatively, when the events occur at a rate below the upper threshold, therapy may be delayed while the IMD performs further analysis. In the example of FIG. 3A, the rate exceeds an upper threshold of 250 bpm and thus an ATP therapy is started at 316.

Figure 3B:
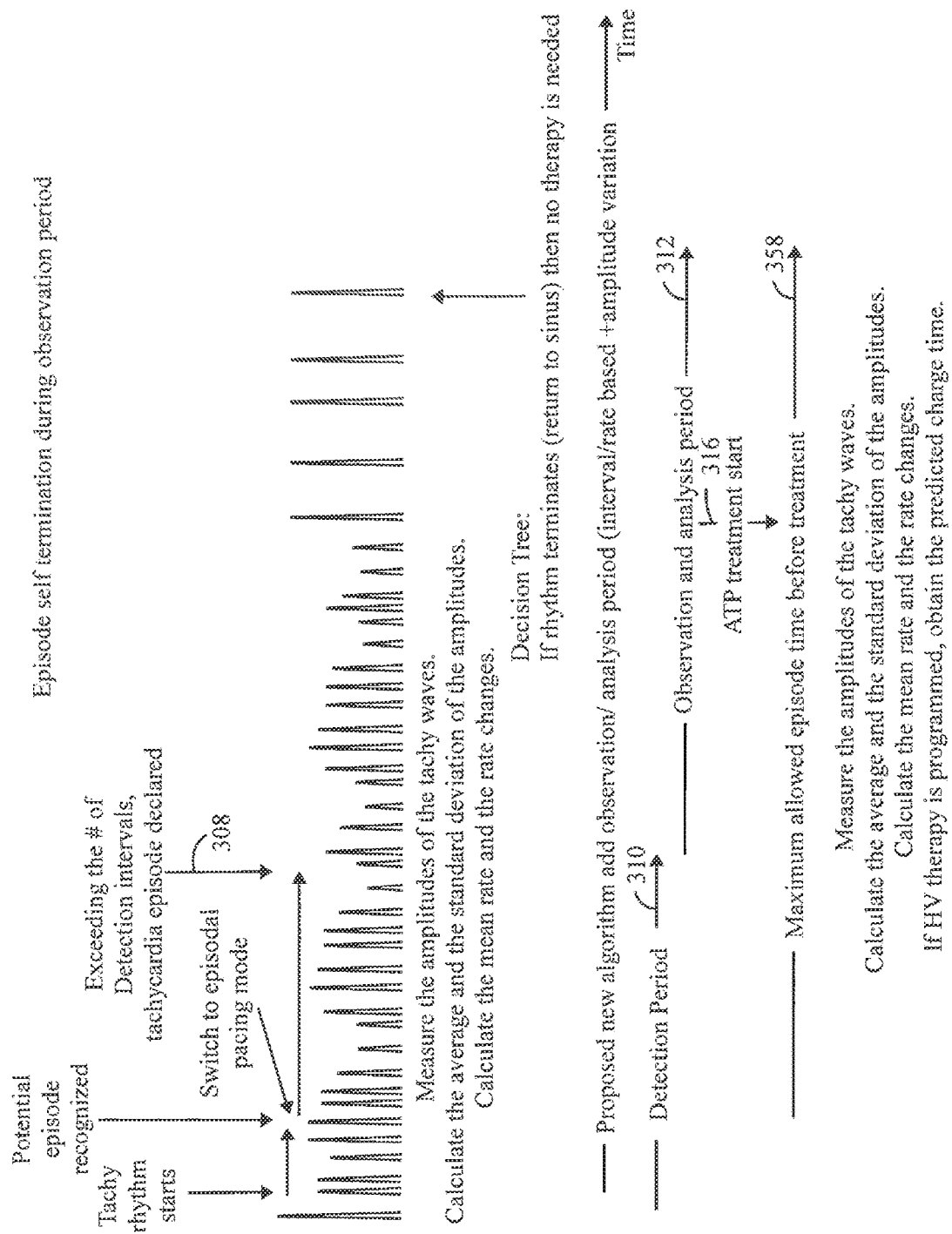
FIG. 3B illustrates an example in which a tachycardia episode self-terminates.

FIG. 3B illustrates an example in which a tachycardia episode self-terminates. When a tachycardia episode self-terminates, no therapy is needed and the observation and analysis period 312 terminates.

Figure 3C:
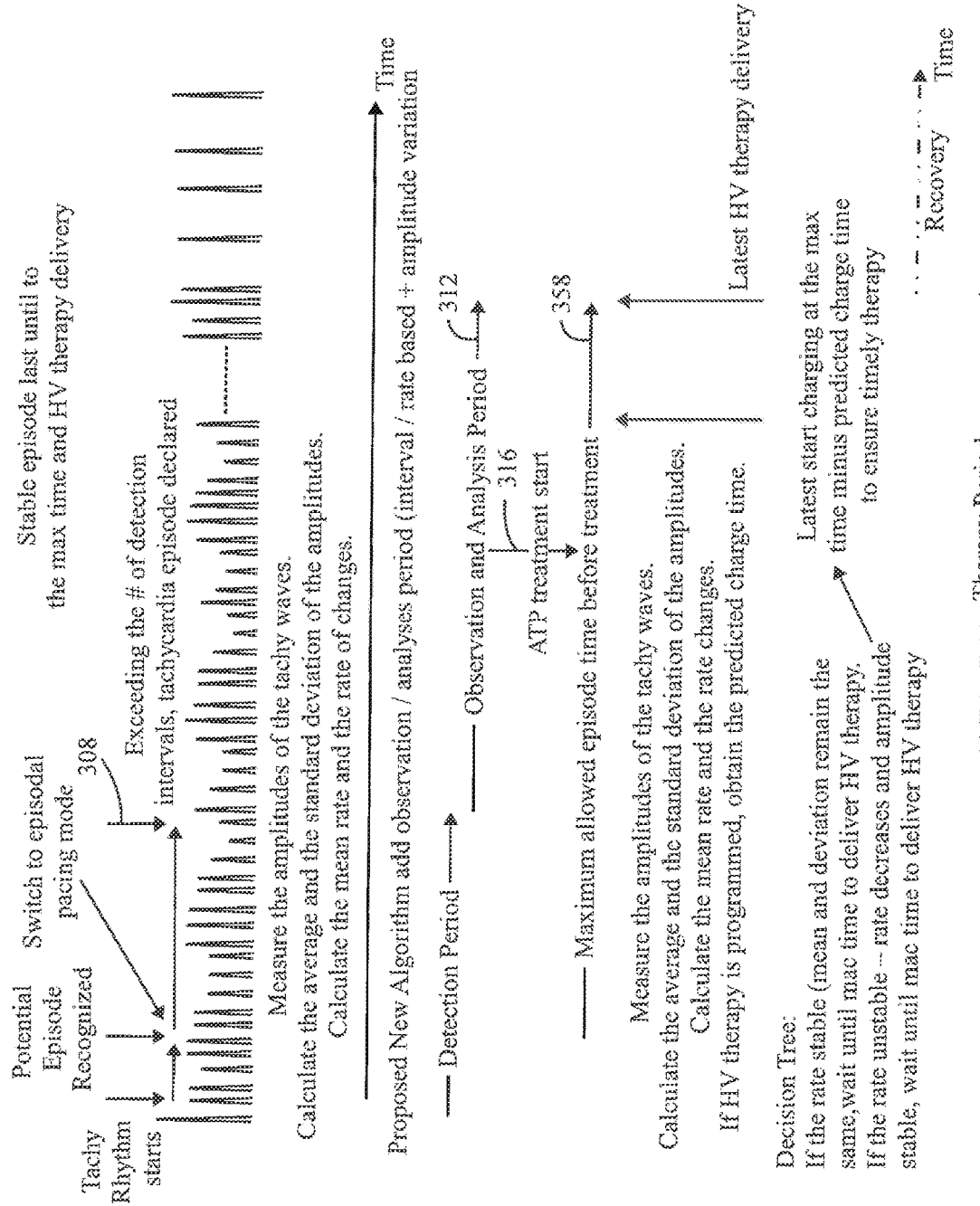
FIG. 3C illustrates an example in which a tachycardia episode continues, and the process determines whether the tachycardia episode exhibits a stable characteristic of interest, such as a stable rate and/or stable amplitude.
Figure 3D:
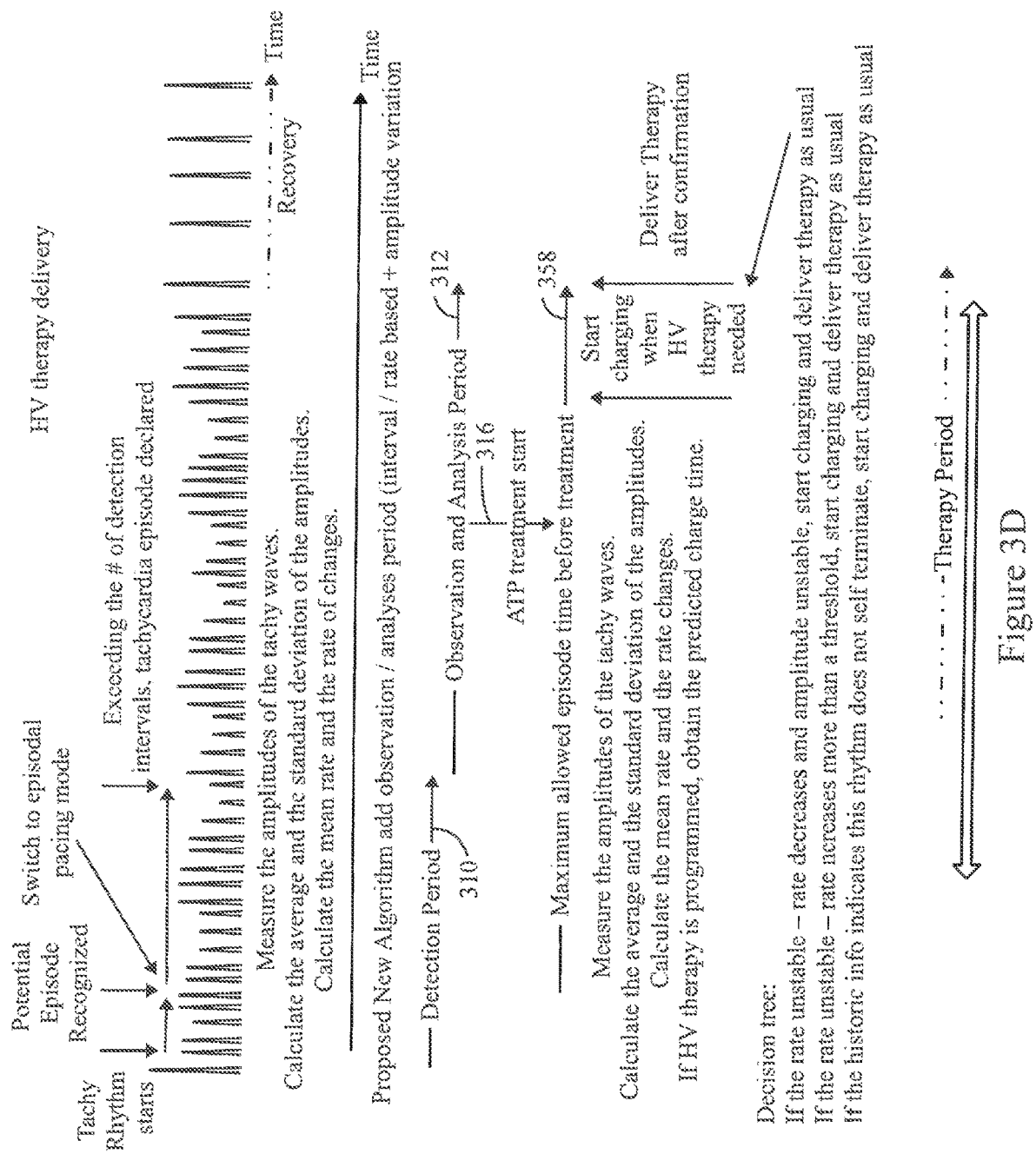
FIG. 3D illustrates a common detection period, followed by a common observation and analysis period in accordance with embodiments herein.
Figure 3E:
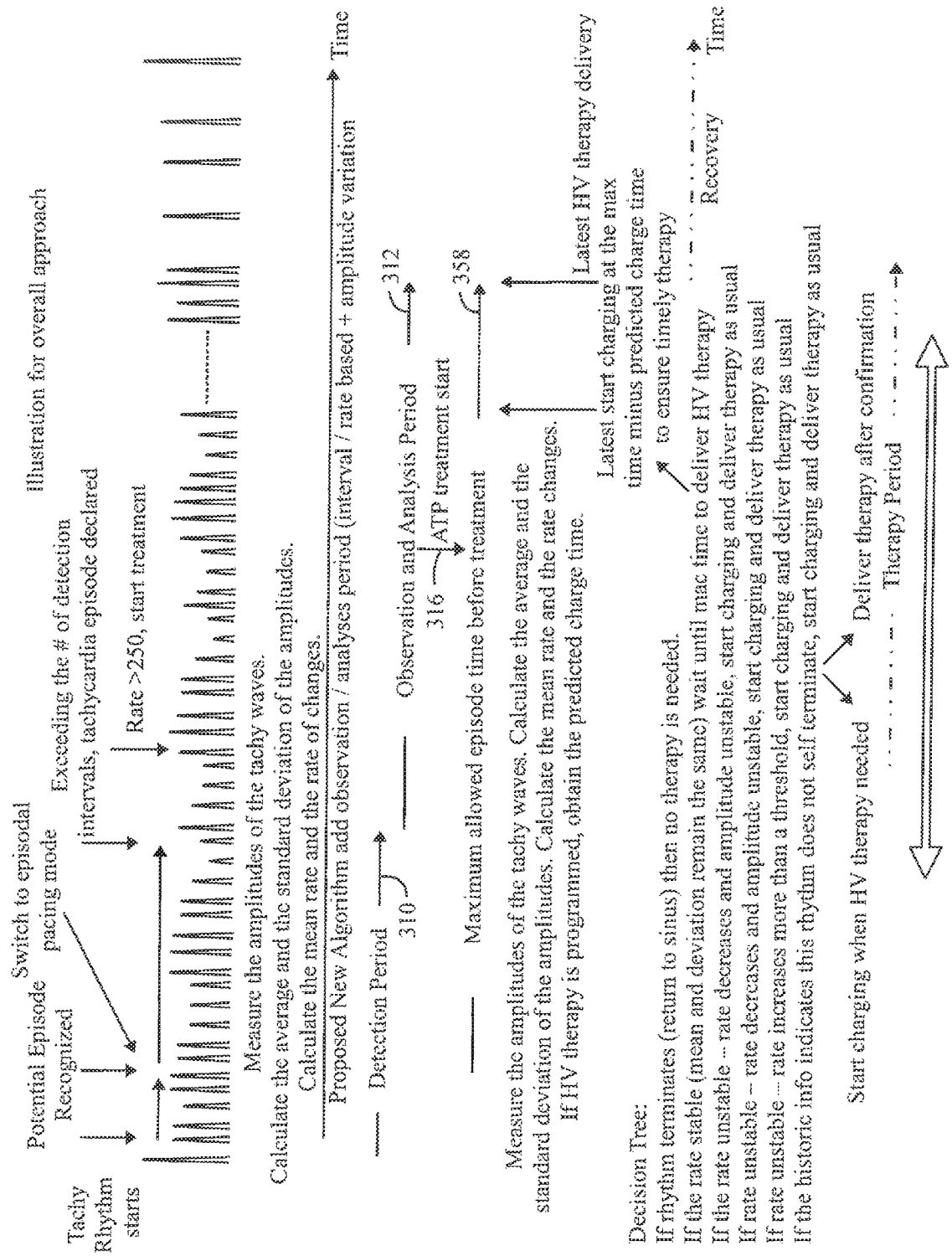
FIG. 3E illustrates a common detection period, followed by a common observation and analysis period in accordance with embodiments herein.

FIG. 3C illustrates an example in which a tachycardia episode continues, and the process determines whether the tachycardia episode exhibits a stable characteristic of interest, such as a stable rate and/or stable amplitude. The stability of the rate and amplitude may be defined based on a degree of variation therein. For example, a threshold or range may be defined in connection with an acceptable amount of variation in the rate and/or amplitude. The process analyzes successive tachycardia events and/or sets/collections of tachycardia events and determines the average, mean, and/or deviation of the rate and amplitude. The process then analyzes changes in the rate mean and deviation over the successive collection of events. The process also analyzes changes in the amplitude, mean, and/or deviation over the successive collection of events. When the rate average, mean, and/or deviation and amplitude average, mean and/or deviation remain within corresponding thresholds or ranges, the IMD declares the episode to have stable rate and stable amplitude. Based thereon, the IMD waits the predetermined (e.g., maximum) time (corresponding to the maximum self-determination duration 358) before delivering an ATP and/or high-voltage therapy. FIG. 3C illustrates the example in which the rate remains stable or the rate is unstable but decreasing, while the amplitude is stable. When either of the foregoing conditions exist, the process waits the predetermined maximum duration for the self-termination period 358.

Continuing with the foregoing example, when the rate mean and/or deviation vary over successive collections of events by an amount that exceeds the corresponding rate mean and/or deviation thresholds and/or ranges, the IMD declares the episode to exhibit an unstable rate. The rate may be unstable in various manners. For example, the rate may be unstable in that the rate decreases over time when comparing earlier collections of events to later collections of events (e.g., going from 330 bpm to 250 bpm). Alternatively, the rate may be unstable in that the rate increases over time when comparing earlier collections of events to later collections of events (e.g., going from 200 bpm to 300 bpm). When the episode exhibits an unstable rate, with the rate decreasing over time (e.g., going from 330 bpm to 25-bpm), while the episode exhibits stable amplitude, the IMD waits the predetermined time before delivering a high-voltage therapy. Additionally or alternatively, when the IMD is programmed to deliver ATP therapy, the ATP therapy is delivered after the ATP therapy delay expires.

Alternatively, when the rate is stable but the amplitude becomes unstable, the IMD may initiate a charging operation and deliver a high voltage shock when the device is ready. A high voltage shock may be desirable as the unstable amplitude may indicate a potential that the device is under sensing fibrillation events. Additionally or alternatively, when the device is programmed to deliver ATP therapy, if the ATP delay expires before the high voltage shock is delivered, the IMD would deliver the ATP therapy.

When the rate is determined to be unstable and decreasing, in combination with an unstable amplitude, the IMD may initiate a charging operation and deliver a high voltage shock when the device is ready. Additionally or alternatively, the IMD may deliver ATP therapy as described herein. When the rate is unstable and increases to a level greater than an upper threshold, the IMD may initiate a charging operation and deliver a high voltage shock when ready. Additionally or alternatively, the IMD may deliver ATP therapy as described herein.

Optionally, historic rhythm information may be utilized to direct the operations of the IMD. For example, the rate and amplitude of the present episode may be identified to be similar to one or more prior episodes as defined by historic rhythm information. The historic rhythm information may indicate whether the prior episodes self-terminate or not. When a present episode is identified to have similar rate and amplitude characteristics to an historic episode that did not self-terminate, the IMD may initiate the charging operation and deliver a high voltage shock and/or ATP therapy as described herein.

Additionally or alternatively, the IMD may apply additional discriminators during the observation and analysis period. For example, one or more discriminators may be utilized to identify a supraventricular tachyarrhythmia (SVT) episode.

Figure 4:
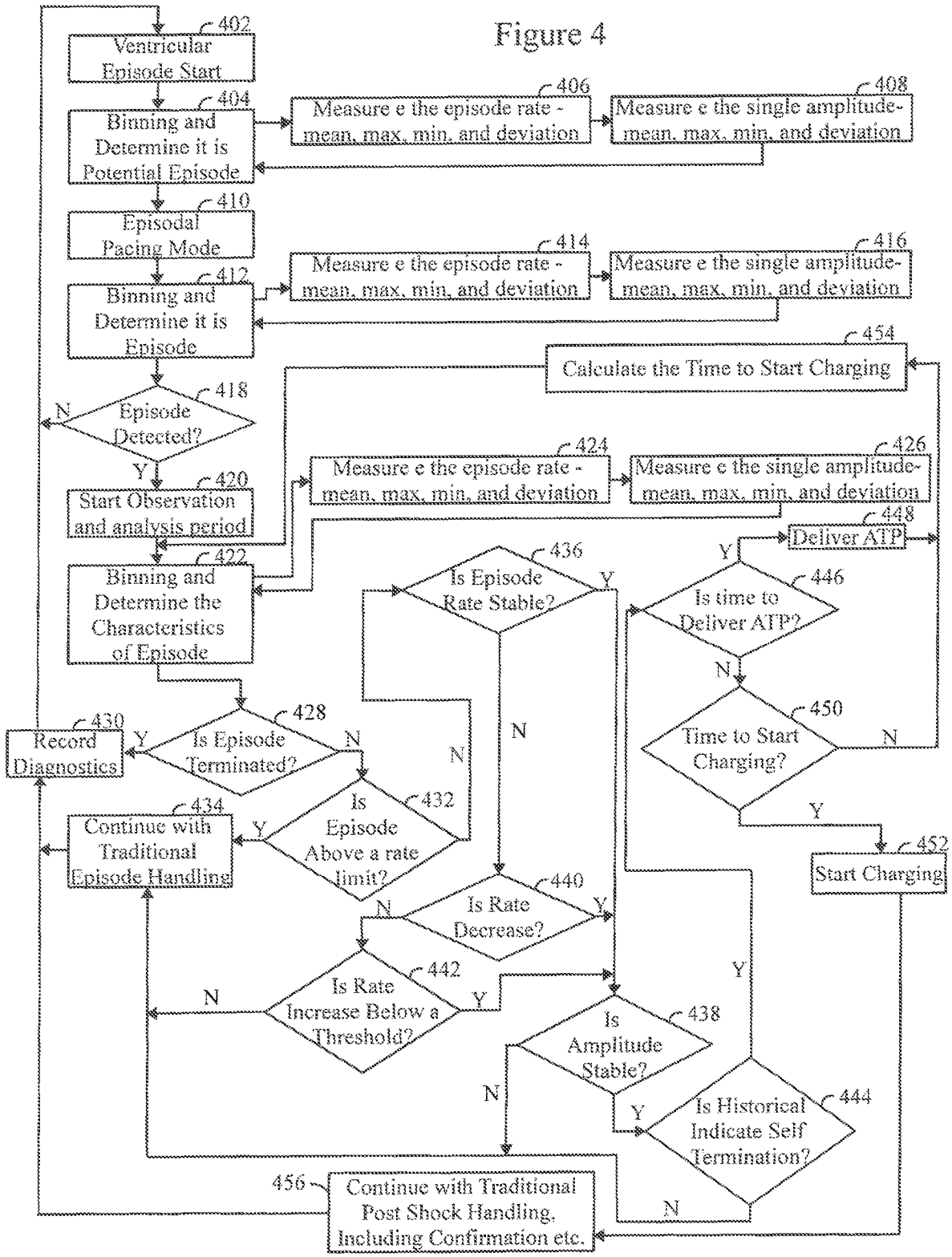
FIG. 4 illustrates a process for determining a treatment time for ventricular arrhythmias in accordance with an embodiment herein.

FIG. 4 illustrates a process for determining a treatment time for ventricular arrhythmias in accordance with an embodiment herein. At 402, one or more processors identify the start of a potential ventricular episode. At 404, the one or more processors collect cardiac events and bin/store the cardiac events for the potential episode identified at 402. By way of example, a predetermined number of cardiac events may be collected at 404. Additionally or alternatively, cardiac events may be measured and collected for a predetermined period of time. At 406 and 408, the one or more processors analyze the cardiac events collected at 404 to measure various characteristics of interest. For example, at 406, the processors measure the event rate and/or interval between successive events. The processors also determine statistical characteristics related to the event rate, such as the mean rate, maximum rate, minimum rate and deviation rate. At 408, the processors measure the amplitudes of the successive events and determine statistical characteristics related to the event amplitude, such as amplitude mean, maximum, minimum and deviation.

At 410, the one or more processors initiate an episode pacing mode. At 412, the one or more processors collect additional cardiac events and bin/store the cardiac events. At 414 and 416, the one or more processors analyze the cardiac events collected at 412 to measure various characteristics of interest. For example, at 414, the processors measure the event rate and/or interval between successive events. The processors also determine statistical characteristics related to the event rate, such as the mean rate, maximum rate, minimum rate and deviation rate. At 416, the processors measure the amplitudes of the successive events and determine statistical characteristics related to the event amplitude, such as amplitude mean, maximum, minimum and deviation.

At 418, the one or more processors determine whether an episode has been detected based on the event related characteristics of interest that are measured and determined at 406, 408, 414 and 416. When no episode is determined, flow returns to 402. When an episode is detected, flow advances to 420. At 420, the one or more processors start the observation and analysis period. At 422, the one or more processors collect cardiac events for a predetermined number of cycles or time and store/bin the cardiac events. At 422, the processors also determine characteristics of interest related to the events. At 424, the processors measure the event rate and/or interval between successive events. The processors also determine statistical characteristics of interest related to the event rate, such as the mean, average, maximum, minimum and deviation rate. At 426, the processors measure the amplitudes of the successive events and determine statistical characteristics related to the event amplitude, such as amplitude mean, average, maximum, minimum and deviation.

At 428, the one or more processors determine whether the episode has terminated. When an episode terminates, flow advances to 430. At 430, the one or more processors record diagnostic information related to the episode. For example, the diagnostic information may include the event and amplitude characteristics that are determined at 406, 408, 414, 416, 424 and 426 (e.g., rate and/or amplitude mean, maximum, minimum and deviation). When an episode is not terminated, flow moves from 428 to 432. At 432, the one or more processors determine whether the event rate exceeds an upper rate threshold (e.g., 250 bpm). When the event rate exceeds the upper rate threshold, flow moves to 434. Otherwise, flow moves to 436. At 436, the one or more processors determine whether the episode exhibits a stable rate. When a stable rate is identified, flow moves to 438. Otherwise, flow moves to 440. When flow moves to 440, the one or more processors determine whether the unstable rate exhibits a decreasing rate or an increasing rate. When the unstable rate exhibits a decreasing rate, flow moves to 438. Otherwise, flow moves to 442. At 442, the one or more processors determine whether the rate increase is still is below an upper threshold. When the rate increase is below an upper threshold, flow moves to 438. Otherwise, flow moves to 434.

At 438, the one or more processors determine whether the amplitude is stable for the episode. When the amplitude is stable, flow moves to 444. Otherwise, flow moves to 434. At 444, the one or more processors access historical episode information to determine whether the characteristics of the present episode match a prior episode that self-terminated. When the present episode exhibits characteristics that match a prior episode that self-terminated, flow moves to 446. Alternatively, when the present episode exhibits characteristics that do not match a self-terminating prior episode, flow moves to 434. At 446, the one or more processors determine whether an ATP therapy timer has timed out. When the ATP therapy timer times out, flow moves to 448 where the IMD delivers an ATP therapy. Alternatively, when the ATP therapy timer has not yet timed out, flow moves to 450 where the IMD determines whether the IMD should start charging a high-voltage delivery circuit. When the high-voltage delivery circuit is to be charged, flow moves to 452. Otherwise, flow moves to 454. At 452, the IMD begins to charge the high-voltage delivery circuit. Thereafter, at 456, the IMD delivers a high voltage shock, followed by post shock processing, such as confirming that the shock is terminated the episode. Thereafter, flow returns to 430 where the processors record diagnostic information related to the episode.

When flow advances from 448 or 450 to 454, the one or more processors calculate a time interval before initiating charge of the high-voltage delivery circuit. Optionally, a predicted charge time may be determined from a dynamic look up table or formula, where the values for the table or formula may be initially set at the time of manufacture or assembly. The values of the dynamic look up table or equation may be updated throughout operation in connection with capacitor maintenance changes and therapy changes.

Optionally, embodiments herein may perform smart charge time management. For example, charging may be started earlier in the process of FIG. 4, before a final decision is made concerning whether an arrhythmia needs high-voltage therapy. A latest start time for the charging operation may be set at a maximum allowed wait time (before delivering therapy) minus a predicted charge time to allow timely therapy. By setting the charge start time relative to the maximum allowed wait time, embodiments herein afford a desired amount of time for the observation period for self-termination, while retaining the ability to deliver therapy quickly when needed. As another example, by waiting until near the end of the maximum allowed wait time before beginning to charge, embodiments herein avoid unnecessary charging operations when an arrhythmia self-terminates at an earlier point in time.

The foregoing operations are repeated until an end of the observation period, A VT/VF therapy is delivered and terminates an arrhythmia or the arrhythmia self-terminates. Thereafter, flow moves to 430 where diagnostic information is recorded as an arrhythmia self-termination (AST) log. The AST log may include information utilized in connection with a self-learning process, in which the IMD learns to recognize certain types of arrhythmias as either self-terminating arrhythmias or non-self-terminating arrhythmias. For example, for each episode, the one or more processors may store, in the AST log, a rate change and/or rate variation exhibited by the ventricular arrhythmia episode during the observation period. The AST log may also store amplitude change and/or variation exhibited by the ventricular arrhythmia episode during the observation period, as well as self-termination information indicating whether the VT arrhythmia self-terminated. The AST log may also store a duration of the VT arrhythmia before self-termination. When a therapy is delivered, the AST log will include the type of therapy that was delivered, which therapy was effective in terminating the VT arrhythmia and the like.

In addition, the one or more processors maintain, in the AST log, a count of the number of different episodes that exhibit similar characteristics. For example, ranges may be defined for rate change/variation and amplitude change/variation. At 430, the AST log is updated to maintain a count of the number of episodes falling within each range. Over time, the one or more processors develop, in the AST log, probabilities that particular types of arrhythmias will self-terminate. For example, 10 arrhythmias may occur over time that have rate and amplitude changes/variations within a common corresponding range. From the 10 arrhythmias, seven may self-terminate, while three required delivery of some type of therapy. From the foregoing information, the AST log may indicate a 70% probability that arrhythmias having rate and amplitude characteristics within the corresponding range will self-terminate. As another example, the AST log may indicate that 9 out of 10 arrhythmias within a select range (e.g., a high risk range) may never terminate. Accordingly, only a 10% probability would exist that arrhythmias having rate and amplitude characteristics in the high risk range would self-terminate.

Figure 5:
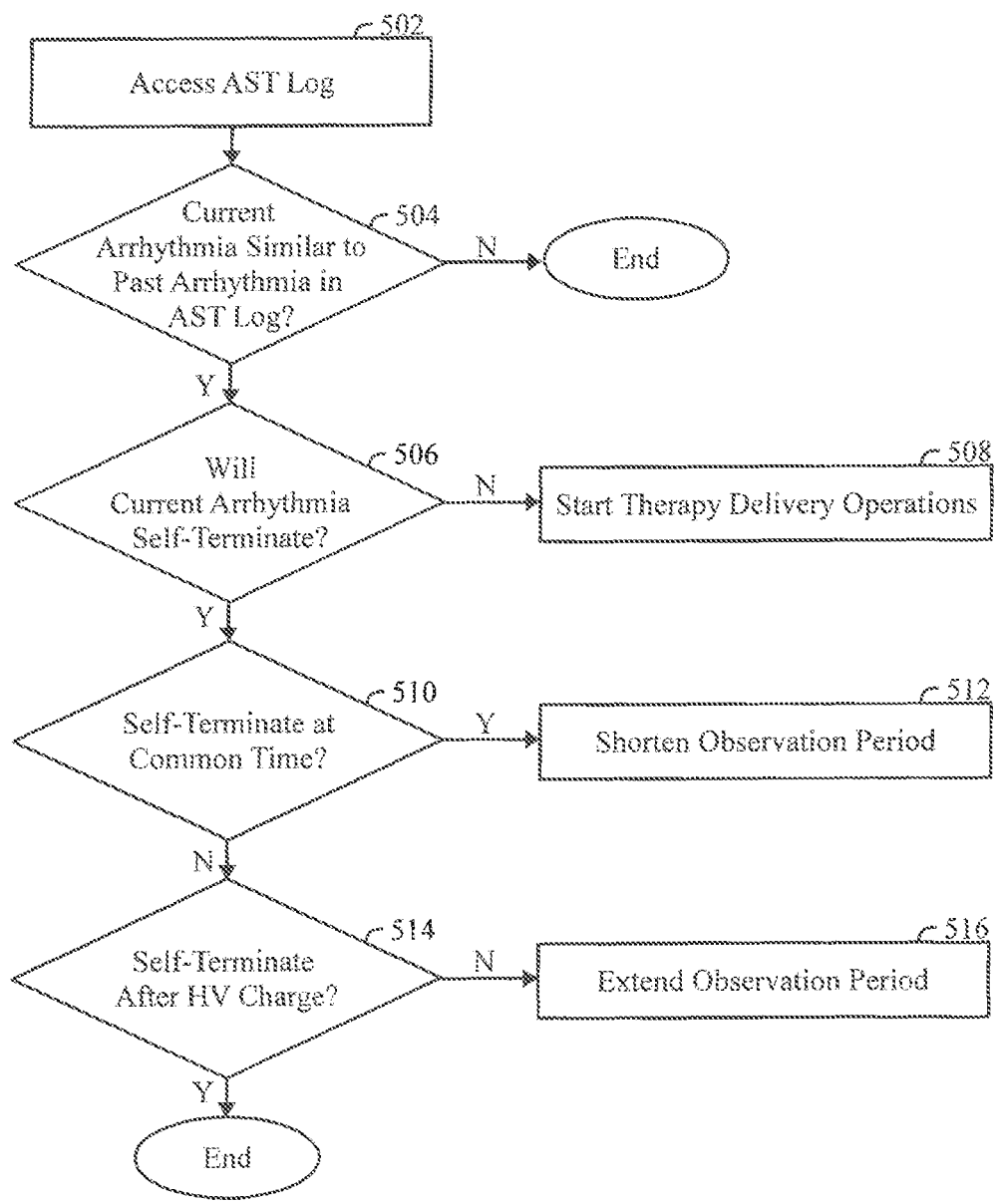
FIG. 5 illustrates a self-learning process for managing self-termination in accordance with embodiments herein.

FIG. 5 illustrates a self-learning process for managing self-termination in accordance with embodiments herein. The operations of FIG. 5 may occur independent of, or at various points in the process of FIG. 4. For example, the operations of FIG. 5 may be performed following the operation at 418 in FIG. 4 when an episode is detected. The operations of FIG. 5 may be performed entirely before continuing to 420 in FIG. 4. Additionally or alternatively, the operations of FIG. 5 may be performed at various points within the process of FIG. 4, such as at 444.

At 502, the one or more processors access the AST log, such as the AST log created at 430 in FIG. 4. The AST log designates various types of arrhythmias based on characteristics thereof. For example, the AST log may designate different types of arrhythmias based on rate and amplitude characteristics of the arrhythmias. The AST log may designate each type of arrhythmia as self-terminating or not.

At 504, the one or more processors review the AST log to determine whether the AST log includes past arrhythmias that exhibit characteristics similar to a present arrhythmia. When the AST log does not include any history of past arrhythmias similar to the present arrhythmia, the process of FIG. 5 terminates and flow returns to FIG. 4 in the manner described above. Alternatively, when a past arrhythmia resembles the present arrhythmia, flow advances to 506. At 506, the one or more processors determine whether the AST log indicates that the arrhythmia is self-terminating. For example, when a particular type of arrhythmia occurs more than a predetermined number of times (e.g., three or more, or some other program value), a self-termination probability may be assigned to the arrhythmia. The probability indicates whether the arrhythmia self-terminating or not.

At 506, the one or more processors may determine whether the present arrhythmia self-terminates based on the probability stored in the AST log for the present type of arrhythmia. For example, a program threshold may be defined, wherein arrhythmias that self-terminate more than 50% of the time are labeled as self-terminating. Optionally, the AST log may store a marker designating the arrhythmia as self-terminating or not self-terminating.

In the present example, the decision at 506 is based on a previously recorded self-termination indicator in the AST log. Optionally, a threshold may be applied at 444 where the threshold is compared to a probability maintained in the AST log.

Alternatively, at 506, when the processors determined that the AST log indicates that the present episode has not historically self-terminated, flow moves to 508. At 508, the one or more processors begin therapy delivery operations. For example, the therapy delivery operations may include delivering ATP therapy in accordance with ATP therapy parameters, starting a high-voltage charging operation (to be followed by a high voltage shock if the arrhythmia does not otherwise terminate) and the like. At 506, when the processors determined that the present episode does historically self-terminate, flow advances to 510.

At 510, the one or more processors determine whether prior similar episodes terminated at a similar point in time. For example, a majority of the prior similar episodes may terminate within a relatively short window of time. When the arrhythmias terminate at a common time, flow moves to 512. At 512, the one or more processors change the duration of the observation period to a shorter observation time period. The shortened duration of the observation period may be preprogrammed. Additionally or alternatively, the shortened duration of the observation period may be based on the time at which the prior similar episodes terminated. For example, the shortened duration of the observation period may be set to be some milliseconds longer or a percentage longer than the amount of time before the prior similar episodes terminated. The resulting observation period and analysis period will sufficiently to cover the self-termination time with its variation. The non-termination episode beyond this time may be belong to another time to episode and require treatment.

At 510, when the prior similar episodes did not terminate at a similar point in time, flow moves to 514. At 514, the one or more processors determine whether the prior similar episodes terminated during the confirmation period following a high-voltage charging operation. If so, flow moves to 516. At 516, the one or more processors extend the observation period. For example, when a particular type of arrhythmia occurs more than a predetermined number of times (e.g., three), when the prior episodes terminate during charging or the confirmation period after high-voltage charging, the observation period may be lengthened by a programmed amount. Optionally, the programmed amount may correspond to a maximum awaiting interval allowed before treatment. At 514, when the prior similar episodes did not terminate after high-voltage charging the process ends.

In accordance with the foregoing operations at 510-516, the duration of the observation period is adjusted based on whether the current ventricular arrhythmia episode is declared to be self-terminating.

As a further example, the AST log may maintain a count of the number of times that a particular type of episode self-terminates at a similar time. For example, when arrhythmias having certain rate and amplitude characteristics self-terminate at a particular time, the observation period may be shortened by an amount based on the amount of time that elapses before the episode self-terminates. Additionally or alternatively, the observation period may be shortened by a programmable amount.

External Device

Figure 6:
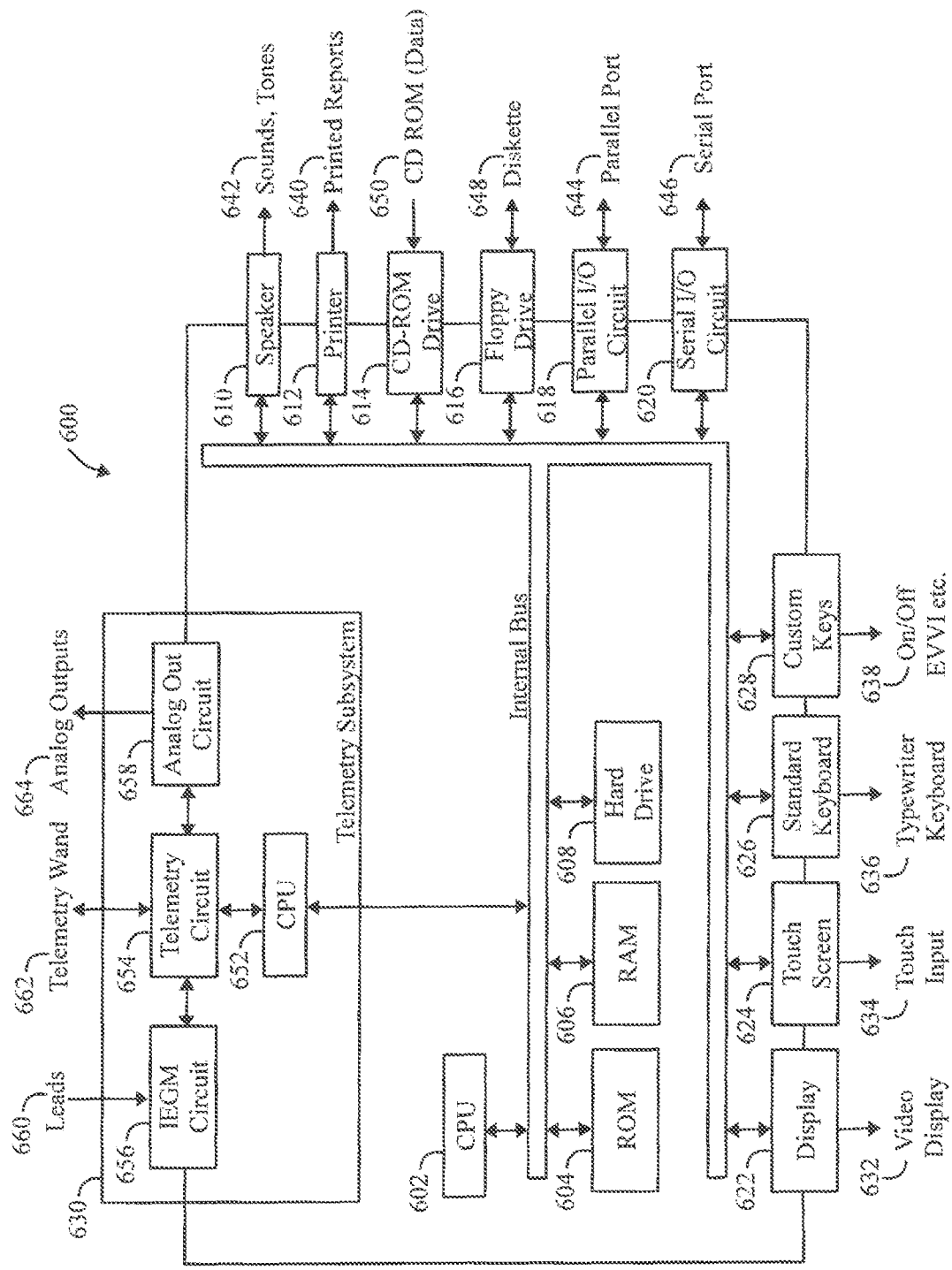
FIG. 6 illustrates a functional block diagram of the external device 600 that is operated in accordance with the processes described herein and to interface with implantable medical devices as described herein.

FIG. 6 illustrates a functional block diagram of the external device 600 that is operated in accordance with the processes described herein and to interface with implantable medical devices as described herein. The external device 600 may perform all or a portion of the sensing, declaring, delaying, analyzing, determining and delivering operations described herein. For example, the external device 600 may be connected to one or more leads having electrodes that sense cardiac events at atrial and/or ventricular sites. The external device 600 may then perform all or a portion of the analysis and determinations herein.

The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds.

The CPU 602 typically includes a microprocessor, a micro-controller, or equivalent control circuitry, designed specifically to control interfacing with the external device 600 and with the IMD 100. The CPU 602 may perform the operations described herein in connection with the various figures. The CPU 602 may include RAM or ROM memory, logic and timing circuitry, state machine circuitry, and I/O circuitry to interface with the IMD 100. The display 622 (e.g., may be connected to the video display 632). The touch screen 624 may display graphic information relating to the IMD 100. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both an IEGM circuit 656 and an analog out circuit 658. The circuit 656 may be connected to leads 660. The circuit 656 is also connected to the implantable leads 114, 116 and 118 to receive and process IEGM cardiac signals as discussed above. Optionally, the IEGM cardiac signals sensed by the leads 114, 116 and 118 may be collected by the IMD 100 and then transmitted, to the external device 600, wirelessly to the telemetry subsystem 630 input.

The telemetry circuit 654 is connected to a telemetry wand 662. The analog out circuit 658 includes communication circuits to communicate with analog outputs 664. The external device 600 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 600 to the IMD 100.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method, comprising:
    sensing electrical cardiac signals, from electrodes located proximate to one or more atrial or ventricular sites, over a period of time that includes a detection period followed by an observation period;
    utilizing one or more processors to perform:
        declaring a ventricular arrhythmia episode and a corresponding VT/VF therapy based on the electrical cardiac signals sensed by the electrodes during at least the detection period;
        delaying delivery of the VT/VF therapy for a self-termination period within the observation period, the self-termination period representing a time period during which the ventricular arrhythmia episode may self-terminate;
        analyzing a stability characteristic of interest (COI) of the ventricular arrhythmia episode from the electrical cardiac signals sensed by the electrodes over at least a portion the observation period;
        determining an end point for the self-termination period, within the observation period, based on the stability COI; and
        delivering the VT/VF therapy when the ventricular arrhythmia episode continues past the end point.

2. The method of claim 1, wherein the analyzing and determining operations occur in response to the declaring of the VT therapy and after the delaying delivery of the VT therapy, such that no anti-tachycardia therapy is delivered following the declaring operation and during the self-termination period.

3. The method of claim 1, wherein the analyzing operation further comprises detecting tachycardia events from the cardiac events, measuring amplitudes of the tachycardia events, and analyzing the stability COI based on the amplitudes.

4. The method of claim 3, wherein the analyzing operation further comprises calculating the stability COI based on at least one of a mean or variance of the amplitudes.

5. The method of claim 1, wherein the analyzing operation further comprises detecting tachycardia events from the cardiac events, measuring rates between the tachycardia events, and analyzing the stability COI based on the rates.

6. The method of claim 1, wherein the determining operation ends the self-termination period when the stability COI exhibits increasing rate instability and initiates an operation to deliver the VT/VF therapy based on the increasing rate instability.

7. The method of claim 1, wherein, when the stability COI is declared stable, the determining operation sets the end point based on a predetermined maximum duration for the self-termination period before delivering the VT/VF therapy.

8. The method of claim 1, wherein the analyzing operation determines whether the stability COI is stable or unstable and increasing or decreasing, the determining operation designating a first end point for the self-termination period when the stability COI exhibits an unstable and decreasing rate in combination with an unstable amplitude.

9. The method of claim 1, further comprising maintaining an arrhythmia self-termination log that is utilized in connection with a self learning process to recognize certain types of arrhythmias as either self-terminating or non-self-terminating.

10. The method of claim 1, wherein the stability COI represents a degree of variation in one or more of an amplitude or rate of tachycardia events.

11. The method of claim 10, further comprising declaring the cardiac events to be unstable based on the stability COI, and in response thereto the determining sets the endpoint to immediately terminate the self termination period and initiate the delivery of the VT/VF therapy.

12. The method of claim 10, further comprising declaring the cardiac events to be stable based on the stability COI, and in response thereto, the determining sets the endpoint to a future point in time based on a predetermined maximum duration for the self termination period.

13. The method of claim 10, wherein the determining includes determining the end point based on the degree of variation in the one or more of an amplitude or rate of tachycardia events.

14. A method, comprising:
sensing electrical cardiac signals, from electrodes located proximate to one or more atrial or ventricular sites, over a period of time that includes a detection period followed by an observation period;
utilizing one or more processors to perform:
declaring a ventricular arrhythmia episode and a corresponding VT/VF therapy based on the electrical cardiac signals during at least the detection period;
delaying delivery of the VT/VF therapy for a self-termination period within the observation period, the self-termination period representing a time period during which the ventricular arrhythmia episode may self-terminate;
analyzing a stability characteristic of interest (COI) from the electrical cardiac signals sensed by the electrodes over at least a portion of the observation period;
determining an end point for the self-termination period, within the observation period, based on the stability COI; and
delivering the VT/VF therapy when the arrhythmia episode continues past the end point;
wherein the analyzing operation further comprises calculating the stability COI based on at least one of a mean or variance of the rates.

15. A method, comprising:
sensing cardiac events, from electrodes located proximate to one or more atrial or ventricular sites, over a period of time that includes a detection period followed by an observation period;
utilizing one or more processors to perform:
declaring a ventricular arrhythmia episode and a corresponding VT/VF therapy based on the cardiac events during at least the detection period;
delaying delivery of the VT/VF therapy for a self-termination period within the observation period, the self-termination period representing a time period during which the ventricular arrhythmia episode may self-terminate;
analyzing a stability characteristic of interest (COI) from the cardiac events sensed over at least a portion the observation period, wherein the stability COI represents a degree of variation in at least one of an amplitude or rate of the tachycardia events, the analyzing operation declaring the tachycardia events to be stable or unstable based on the stability COI;
determining an end point for the self-termination period, within the observation period, based on the stability COI; and
delivering the VT/VF therapy when the VT/VF arrhythmia episode continues past the end point.

16. The method of claim 15, wherein the stability COI is declared unstable when the degree of variation corresponds to a rate variation that exceeds a rate threshold, the method further comprising determining whether the rate variation represents increasing or decreasing rate instability, the determining operation setting the end point based on a predetermined maximum duration for the self-termination period before delivering the VT/VF therapy when the stability COI exhibits the decreasing rate instability.

17. The method of claim 15, wherein the stability COI is declared unstable when the stability COI indicates the degree of variation in the amplitude exceeds an amplitude threshold, the method further comprising determining whether the amplitude exhibits increasing or decreasing amplitude instability, wherein the determining operation designating the end point for the self-termination period when the stability COI exhibits the increasing amplitude instability and initiates an operation to deliver the VT/VF therapy.

18. An implantable medical device, comprising:
electrodes configured to be located proximate to one or more atrial or ventricular sites, the electrodes configured to sense electrical cardiac signals over a period of time that includes a detection period followed by an observation period;
memory to store program instructions; and
one or more processors that, when executing the program instructions:
declare a ventricular arrhythmia episode and a corresponding VT therapy based on the electrical cardiac signals sensed by the electrodes during at least the detection period;
delay delivery of the VT therapy for a self-termination period within the observation period, the self-termination period representing a time period during which the ventricular arrhythmia episode may self-terminate;
analyze a stability characteristic of interest (COI) of the ventricular arrhythmia episode from the electrical cardiac signals sensed by the electrodes over at least a portion the observation period;
determine an end point for the self-termination period, within the observation period, based on the stability COI; and
deliver the VT/VF therapy when the ventricular arrhythmia episode continues past the end point.

19. The device of claim 18, wherein the one or more processors are configured to perform the analyze and determine operations occur in response to the declaring of the VT/VF therapy and after the delaying delivery of the VT/VF therapy, such that no anti-tachycardia therapy is delivered following the declaring operation and during the self-termination period.

20. The device of claim 18, wherein the one or more processors are further configured to detect tachycardia events from the cardiac events, measure amplitudes of the tachycardia events, and analyze the stability COI based on the amplitudes.

21. The device of claim 18, wherein the one or more processors are further configured to calculate the stability COI based on at least one of a mean or variance of the amplitudes.

22. The device of claim 18, wherein the one or more processors are further configured to detect tachycardia events from the cardiac events, measure rates between the tachycardia events, and analyze the stability COI based on the rates.

23. The device of claim 18, wherein the one or more processors are configured to determine whether past and current ventricular arrhythmia episodes are similar and based thereon declaring the current ventricular arrhythmia episode to be self-terminating.

24. The device of claim 23, wherein the one or more processors adjust a duration of the observation period based on whether the current ventricular arrhythmia episode is declared to be self-terminating.

25. The device of claim 18, wherein the stability COI represents a degree of variation in one or more of an amplitude or rate of tachycardia events.

26. The device of claim 25, wherein the determining includes determining the end point based on the degree of variation in the one or more of an amplitude or rate of tachycardia events.

27. The device of claim 18, wherein the one or more processors are further configured to declare the cardiac events to be unstable based on the stability COI, and in response thereto to set the endpoint to immediately terminate the self termination period and initiate the delivery of the VT/VF therapy.

28. The device of claim 18, wherein the one or more processors are further configured to declare the cardiac events to be stable based on the stability COI, and in response thereto, to set the endpoint to a future point in time based on a predetermined maximum duration for the self termination period.

* * * * *